(12) United States Patent
Goubau et al.

(10) Patent No.: US 8,858,644 B2
(45) Date of Patent: Oct. 14, 2014

(54) ORTHOPAEDIC IMPLANT FOR ARTHROPLASTY OF THE FINGERS

(75) Inventors: Jean Goubau, Loppem (BE); Xavier Martinache, Reims (FR); Michaël Papaloïzos, Geneva (CH); Philippe Bellemere, Nantes (FR); Thierry Dreano, Rennes (FR); Bernard Prandi, Rennes (FR); Pierre Siret, Talensac (FR); Alain Tchurukdichian, Dijon (FR)

(73) Assignee: Memometal Technologies (FR)

( * ) Notice: Subject to any disclaimer, the term of this patent is extended or adjusted under 35 U.S.C. 154(b) by 0 days.

(21) Appl. No.: 12/918,174

(22) PCT Filed: Jan. 8, 2010

(86) PCT No.: PCT/FR2010/000010
§ 371 (c)(1), (2), (4) Date: Nov. 22, 2010

(87) PCT Pub. No.: WO2010/079288
PCT Pub. Date: Jul. 15, 2010

(65) Prior Publication Data
US 2011/0257755 A1    Oct. 20, 2011

(30) Foreign Application Priority Data
Jan. 8, 2009    (FR) ..................... 09 00054

(51) Int. Cl.
*A61F 2/42* (2006.01)
*A61F 2/30* (2006.01)

(52) U.S. Cl.
CPC ..... *A61F 2/4241* (2013.01); *A61F 2002/30327* (2013.01); *A61F 2002/30131* (2013.01); *A61F 2002/30772* (2013.01); *A61F 2002/4251* (2013.01); *A61F 2/4225* (2013.01); *A61F 2002/30166* (2013.01); *A61F 2002/30332* (2013.01); *A61F 2002/4243* (2013.01); *A61F 2002/30616* (2013.01); *A61F 2002/30594* (2013.01)
USPC ....................................... 623/21.15

(58) Field of Classification Search
USPC .......... 623/20.11, 20.14, 20.21, 20.24, 20.26, 623/20.31, 20.34, 20.36, 21.15–21.17, 623/23.39
See application file for complete search history.

(56) References Cited

U.S. PATENT DOCUMENTS 3,462,765 A    8/1969    Swanson
3,466,669 A    9/1969    Flatt
(Continued)

FOREIGN PATENT DOCUMENTS

DE    2424537 A1    12/1974
DE    19651546 A1    6/1997
DE    29721522 U1    2/1998
(Continued)

*Primary Examiner* — Bruce E Snow
*Assistant Examiner* — Brian Dukert
(74) *Attorney, Agent, or Firm* — Lerner, David, Littenberg, Krumholz & Mentlik, LLP (57) ABSTRACT

An orthopaedic implant used in arthroplasty of the fingers comprises a first element for a proximal phalanx and a second element for an adjacent distal phalanx, each element having a respective stem for implantation in the bone and an interphalangeal articulation head, the head of the first element having a biconvex surface of articulation, with a central valley, and the head of the second element having a biconcave surface of articulation designed to cooperate with said convex surface and comprising a central crest. At rest, the surfaces are congruent in the frontal plane of the articulation in the area of the condyles and non-congruent in the sagittal plane.

20 Claims, 4 Drawing Sheets

(56) References Cited

U.S. PATENT DOCUMENTS

| | | |
|---|---|---|
| 3,651,521 A | 3/1972 | Devas |
| 3,681,786 A | 8/1972 | Lynch |
| 3,739,403 A | 6/1973 | Nicolle |
| 3,745,590 A | 7/1973 | Stubstad |
| 3,760,427 A | 9/1973 | Schultz |
| 3,875,594 A | 4/1975 | Swanson |
| 3,909,853 A | 10/1975 | Lennox |
| 3,924,276 A | 12/1975 | Eaton |
| 3,991,425 A | 11/1976 | Martin et al. |
| 4,011,603 A | 3/1977 | Steffee |
| 4,059,854 A | 11/1977 | Laure |
| 4,158,893 A | 6/1979 | Swanson |
| 4,180,871 A | 1/1980 | Hamas |
| 4,193,139 A | 3/1980 | Walker |
| 4,231,121 A | 11/1980 | Lewis |
| 4,242,759 A | 1/1981 | White |
| 4,250,873 A | 2/1981 | Bonnet |
| 4,276,660 A | 7/1981 | Laure |
| 4,304,011 A | 12/1981 | Whelan, III |
| 4,352,212 A | 10/1982 | Greene et al. |
| 4,451,254 A | 5/1984 | Dinius et al. |
| 4,453,930 A | 6/1984 | Child |
| 4,655,778 A | 4/1987 | Koeneman |
| 4,685,919 A | 8/1987 | Niwa et al. |
| 4,725,280 A | 2/1988 | Laure |
| 4,732,564 A | 3/1988 | Potucek et al. |
| 4,865,605 A * | 9/1989 | Dines et al. ............... 623/19.14 |
| 4,871,367 A | 10/1989 | Christensen et al. |
| 4,944,758 A | 7/1990 | Bekki et al. |
| 4,955,916 A | 9/1990 | Carignan et al. |
| 4,959,065 A | 9/1990 | Arnett et al. |
| 5,011,497 A | 4/1991 | Persson et al. |
| 5,037,440 A | 8/1991 | Koenig |
| 5,047,059 A | 9/1991 | Saffar |
| 5,092,896 A | 3/1992 | Meuli et al. |
| 5,108,443 A | 4/1992 | Branemark |
| 5,133,761 A | 7/1992 | Krouskop |
| 5,147,386 A | 9/1992 | Carignan et al. |
| 5,228,455 A | 7/1993 | Barcel |
| 5,290,314 A | 3/1994 | Koch et al. |
| 5,358,529 A * | 10/1994 | Davidson .................... 623/20.19 |
| 5,387,244 A | 2/1995 | Breard |
| 5,405,399 A | 4/1995 | Tornier |
| 5,405,400 A | 4/1995 | Linscheid et al. |
| 5,405,401 A | 4/1995 | Lippincott, III et al. |
| 5,413,609 A | 5/1995 | Nicol et al. |
| 5,425,777 A | 6/1995 | Sarkisian et al. |
| 5,458,647 A | 10/1995 | Brochier et al. |
| 5,458,648 A | 10/1995 | Berman et al. |
| 5,480,447 A | 1/1996 | Skiba |
| 5,507,822 A | 4/1996 | Bouchon et al. |
| 5,522,900 A | 6/1996 | Hollister |
| 5,522,903 A | 6/1996 | Sokolow et al. |
| 5,549,690 A | 8/1996 | Hollister et al. |
| 5,645,605 A | 7/1997 | Klawitter |
| 5,674,297 A | 10/1997 | Lane et al. |
| 5,683,466 A | 11/1997 | Vitale |
| 5,702,458 A * | 12/1997 | Burstein et al. ............ 623/20.31 |
| 5,702,469 A | 12/1997 | Whipple et al. |
| 5,702,472 A | 12/1997 | Huebner |
| 5,725,585 A | 3/1998 | Zobel |
| 5,728,163 A | 3/1998 | Maksene |
| 5,782,927 A | 7/1998 | Klawitter et al. |
| 5,824,095 A | 10/1998 | Di Maio, Jr. et al. |
| 5,938,700 A | 8/1999 | Lippincott, III |
| 5,976,134 A | 11/1999 | Huebner |
| 5,976,139 A | 11/1999 | Bramlet |
| 5,984,970 A | 11/1999 | Bramlet |
| 5,984,971 A | 11/1999 | Faccioli et al. |
| 6,053,945 A | 4/2000 | O'Neil et al. |
| 6,099,571 A | 8/2000 | Knapp |
| 6,159,247 A | 12/2000 | Klawitter et al. |
| 6,183,474 B1 | 2/2001 | Bramlet et al. |
| 6,284,001 B1 | 9/2001 | Knapp |
| 6,352,560 B1 | 3/2002 | Poeschmann et al. |
| 6,423,097 B2 | 7/2002 | Rauscher |
| 6,454,808 B1 | 9/2002 | Masada |
| 6,475,242 B1 | 11/2002 | Bramlet |
| 6,506,215 B1 | 1/2003 | Letot et al. |
| 6,572,534 B1 | 6/2003 | Milbocker et al. |
| 6,622,864 B1 | 9/2003 | Debbs et al. |
| 6,682,565 B1 | 1/2004 | Krishnan |
| 6,689,169 B2 | 2/2004 | Harris |
| 6,695,844 B2 | 2/2004 | Bramlet et al. |
| 6,699,292 B2 * | 3/2004 | Ogilvie et al. ............ 623/21.15 |
| 6,811,568 B2 | 11/2004 | Minamikawa |
| 6,869,449 B2 | 3/2005 | Ball et al. |
| 6,887,169 B2 | 5/2005 | Whitehill et al. |
| 6,984,235 B2 | 1/2006 | Huebner |
| 7,004,946 B2 | 2/2006 | Parker et al. |
| 7,025,789 B2 | 4/2006 | Chow et al. |
| 7,041,106 B1 | 5/2006 | Carver et al. |
| 7,182,787 B2 | 2/2007 | Hassler et al. |
| 7,347,130 B2 | 3/2008 | Pham et al. |
| 7,491,209 B2 | 2/2009 | Mueller et al. |
| 7,507,252 B2 | 3/2009 | Lashinski et al. |
| 7,611,538 B2 | 11/2009 | Belliard et al. |
| 7,641,696 B2 | 1/2010 | Ogilvie et al. |
| D610,686 S | 2/2010 | Klawitter et al. |
| D619,718 S | 7/2010 | Gannoe et al. |
| 7,780,737 B2 | 8/2010 | Bonnard et al. |
| 7,803,162 B2 | 9/2010 | Marnay et al. |
| 7,837,738 B2 | 11/2010 | Reigstad et al. |
| 7,837,739 B2 | 11/2010 | Ogilvie |
| 7,857,851 B2 | 12/2010 | Zannis et al. |
| 7,896,919 B2 | 3/2011 | Belliard et al. |
| 7,976,580 B2 | 7/2011 | Berger |
| 8,012,217 B2 | 9/2011 | Strzepa et al. |
| 8,021,431 B1 | 9/2011 | Townley |
| 8,034,116 B2 | 10/2011 | Vander Meulen et al. |
| 8,043,375 B2 | 10/2011 | Strzepa et al. |
| 8,070,786 B2 | 12/2011 | Huebner et al. |
| 8,088,168 B2 | 1/2012 | Hassler et al. |
| 8,092,530 B2 | 1/2012 | Strzepa et al. |
| 8,100,983 B2 | 1/2012 | Schulte |
| 8,133,283 B2 | 3/2012 | Wilson |
| 8,152,847 B2 | 4/2012 | Strzepa et al. |
| 8,167,952 B2 | 5/2012 | Graham et al. |
| 8,167,953 B2 | 5/2012 | Warburton |
| 8,177,842 B2 | 5/2012 | Strzepa et al. |
| 8,226,721 B2 | 7/2012 | Belliard et al. |
| 8,231,625 B2 | 7/2012 | Graham et al. |
| 8,292,966 B2 | 10/2012 | Morton |
| 8,303,666 B2 | 11/2012 | Vanasse |
| 8,343,228 B2 | 1/2013 | Graham |
| 8,366,785 B1 | 2/2013 | Townley |
| 8,377,142 B2 | 2/2013 | Trail et al. |
| 8,394,097 B2 | 3/2013 | Peyrot et al. |
| 8,414,583 B2 | 4/2013 | Prandi et al. |
| 8,475,456 B2 | 7/2013 | Augoyard et al. |
| 8,491,663 B2 | 7/2013 | Lindner et al. |
| 8,506,641 B2 | 8/2013 | Graham et al. |
| 2003/0040805 A1 * | 2/2003 | Minamikawa ............ 623/23.46 |
| 2008/0154385 A1 | 6/2008 | Trail et al. |
| 2010/0010637 A1 | 1/2010 | Pequignot |
| 2011/0106269 A1 | 5/2011 | Warburton |

FOREIGN PATENT DOCUMENTS

| | | |
|---|---|---|
| DE | 19820748 A | 11/1999 |
| DE | 19925529 A1 | 12/2000 |
| EP | 0524874 A1 | 1/1993 |
| EP | 1632200 A1 | 3/2006 |
| EP | 1992309 A1 | 11/2008 |
| FR | 2670109 A1 | 6/1992 |
| FR | 2680967 A1 | 3/1993 |
| FR | 2734150 A | 11/1996 |
| FR | 2736818 A1 | 1/1997 |
| FR | 2736818 A1 | 1/1997 |
| FR | 2743717 A1 | 7/1997 |
| FR | 2770770 A1 | 5/1999 |
| FR | 2912051 A1 | 8/2008 |
| GB | 2049435 A | 12/1980 |
| GB | 2251795 A | 7/1992 |

(56) References Cited

FOREIGN PATENT DOCUMENTS

| | | | |
|---|---|---|---|
| GB | 2308068 A | 6/1997 | |
| JP | 10-513371 | 12/1998 | |
| JP | 11-332893 A | 12/1999 | |
| JP | 2004520873 A | 7/2004 | |
| JP | 2005052629 A | 3/2005 | |
| JP | 2008284348 A | 11/2008 | |
| WO | 9623460 A1 | 8/1996 | |
| WO | 0243627 A2 | 6/2002 | |

* cited by examiner

ORTHOPAEDIC IMPLANT FOR ARTHROPLASTY OF THE FINGERS

CROSS REFERENCE TO RELATED APPLICATIONS

This application is the US national phase of PCT application PCT/FR2010/000010, filed 8 Jan. 2010, published 15 Jul. 2010 as 2010/079288, and claiming the priority of French patent application 0900054 itself filed 8 Jan. 2009, whose entire disclosures are herewith incorporated by reference.

BACKGROUND OF THE INVENTION

The present invention relates to an orthopedic implant used in arthroplasty of the fingers, comprising a first element for a proximal phalanx and a second element for an adjacent distal phalanx.

A proximal phalanx is to be understood to mean a phalanx located on the body side or member side (hand or foot) in question, and a distal phalanx is to be understood to mean a phalanx located toward the outside of this member, according to the orientation rules conventionally adopted in anatomy that will moreover be used below.

The invention also relates to a method for installing such an implant.

The invention finds one particularly important, although not exclusive, application in the medical field of proximal interphalangeal joint prostheses for the hand (known in the field by the initials PIP).

However, it can also and in particular be used advantageously for interphalangeal finger joint prostheses for the thumb (thumb IP) or for distal interphalangeal prostheses (DIP) for the hand or foot, by simple geometric adaptation to the bone sites in question.

There are already known interphalangeal joint prostheses comprising first and second elements, each element having a stem for implantation in the bone and a complementary interphalangeal pivot head.

For example, there is known (EP 1 339 362) [U.S. Pat. No. 6,699,292] an implant comprising a first element provided with a head having a convex bicondylar pivot surface having a central valley, and a second element provided with a complementary head having a biconcave pivot surface designed to cooperate with the convex surface so that there is a congruence between these surfaces in the sagittal plane.

Congruence is to be understood to mean the fact of coinciding or of fitting perfectly with one another in the sagittal plane.

The congruence in the sagittal plane therefore means that the point of contact between the two articular surfaces in this plane always passes through the same line of surface contact during movement.

It should be recalled that a sagittal or parasagittal plane is a plane parallel to the median plane when the human body is in the upright position.

Such an arrangement, although it allows good guidance of the joint, is sometimes prejudicial to the service life of the prosthesis. This is because it may give cause jamming and thus a failure of the prosthesis in up to 20% of cases, depending on the surgeon carrying out the procedure; in addition, it causes significant wear on the articular surfaces of the prosthesis, requiring a new operation.

Prostheses are also known (EP 0 572 339) [U.S. Pat. No. 5,405,399] having barrel-shaped bicondylar surfaces with different radii of curvature.

Here again, this type of implant that is used in particular as a shoulder prosthesis, poses problems of wear and is moreover not very suitable for joints of small size such as those of the fingers.

In order to attempt to alleviate these drawbacks, prostheses made from bioceramic, for the fingers or toes, have been envisaged (DE 198 207 48).

Although such prostheses are more resistant to wear, they nevertheless present a risk of shattering and are also complex to install.

SUMMARY OF THE INVENTION

The object of the present invention is to provide an orthopedic implant and a method that satisfy the practical requirements better than those known previously, in particular in that it wears very little despite numerous joint movements, and in that it is very easy to install while adapting to the constraints associated with the subsequent functions of arthroplastic joints.

It is moreover of low cost and allows a high degree of modularity, that is to say a high degree of variance in terms of size.

To this end, the present invention proposes an orthopedic implant used in arthroplasty of the fingers, comprising a first element for a proximal phalanx and a second element for an adjacent distal phalanx, each element having a respective stem for implantation in the bone and an interphalangeal pivot head, the head of the first element having a biconvex condylar pivot surface, having a central valley, and the head of the second element having a biconcave pivot surface designed to fig generally complementarily with the biconvex surface and having a central ridge, characterized in that the surfaces at rest are congruent in the frontal plane of the pivot in the area of the condyles and are not congruent in the sagittal plane.

At rest is to be understood to mean an absence of external pressure on the surfaces of the pivot.

The congruence in the frontal plane in the area of the condyles means that the zone of contact between the two articular surfaces is formed by two horizontal lines that pass vertically over the surface during movement.

Surprisingly, this congruence in the frontal plane associated with no congruence in the sagittal plane ensures in the presence of articular fluid an excellent lubrication of the joint during movement and thus considerably limits wear on the articular surfaces and stiffening.

In advantageous embodiments, use is moreover made of one and/or the other of the following arrangements:

- the radii of curvature (R1, R'1) of the condyles of the biconvex surface of the first element are identical to the radii of curvature (R2, R'2) of the respective biconcave surface of the second element in the frontal plane, the radius of curvature (R3) of the proximal surface of the first element being smaller than the radius of curvature (R4) of the respective distal surface of the second element in the sagittal plane.

Radius of curvature in the frontal plane is to be understood to mean the radius of the curve formed by the intersection of the pivot surface with a transverse plane orthogonal to the surface of the head;

the radii of curvature are such that R1=R'1=R2=R'2;

the material of the heads is designed to allow the heads to cooperate by friction along a line of friction in the frontal plane in the absence of longitudinal pressure and along a crush zone in the frontal plane in the event of longitudinal pressure.

Longitudinal pressure is to be understood to mean a pressure exerted in the longitudinal direction of one or of both phalanxes in question. In other words, this arrangement makes it possible in particular to obtain a maximum congruence under load, transforming the two lines of contact mentioned above into a strip of contact that thus distributes the forces and further reduces in a surprising manner wear on the articular surfaces;

- the material of the biconvex surface of the head of the first element is a flexible polymer material having a Young's modulus E≤30 Gpa.

The two articular surfaces are thus of different rigidity, the most flexible material that is most subject to wear being on the condyle side.

It will be noted in this regard that, since the condylar surface is in general and by design thicker than the distal surface, this permits a lesser deformation of the flexible material.

Furthermore, since the distal surface passes over a large part of the condylar surface, between the straight position and the flexed position, there is thus a better distribution of wear.

A compromise is thus obtained between a very high elasticity close to that of anatomical cartilage and a greater rigidity so as to limit the deformation and the long-term wear.

Advantageously, it may also be the material known by the name CFR PEEK, these initials referring to Carbon fiber reinforced polyetheretherketone having a Young's modulus of around 18 Gpa;

- the Young's modulus of the bicondylar surface is E≤2 Gpa. More specifically and in a nonlimiting manner, the flexible material is a polyethylene known by the name UHMWPE (these initials referring to ultra high molecular weight polyethylene) with E≤1 Gpa;
- the respective facing surfaces of the heads of the two elements placed in contact define an intercondylar space of non-zero volume along the entire length of the central valley, allowing an improved lubrication of the joint between the heads.

Such an intercondylar space for example of between 15 mm³ and 30 mm³, for example 25 mm³, makes it possible to further improve lubrication of the joint, the contact between the articular surfaces at this location therefore being non-congruent;

- in the frontal plane, the valley of the bicondylar head of the first element has a radius of curvature R5, the ridge of the biconcave surface of the second element having for its part a radius of curvature R6>R5;
- the implantation stems have the shape of a polygonal post that is proportioned so as to be received inside the medullary cavity of a phalanx and are provided with an end stop to prevent them from being excessively pushed in.

Advantageously, the material and the shape of the stem have an effective modulus of elasticity or Young's modulus E≤30 GPa.

The effective or apparent Young's modulus is to be understood to mean an overall Young's modulus of the stem having a behavior identical to that of a material that intrinsically has this Young's modulus.

More specifically, it is possible to provide two apparent stiffnesses of different stems depending on the patients, i.e. a rigid stem for young patients (i.e. around 20 GPa) and a more flexible stem for elderly patients (i.e. around 5 to 6 GPa);

- at least one implantation stem has a shape that is at least partially open in the dorsal-palmar plane;
- at least one implantation stem has an H-shaped, U-shaped or V-shaped cross-section and/or has a duckbill-shaped slot or a recessed semicylindrical shape on the palmar side or a half-tube shape.

Advantageously, the stems are open and/or are covered with a partial or full osseointegrating coating to improves anchoring;

- since the implantation stems of the elements are removable relative to the respective heads, they comprise means for attachment to the heads;
- the attachment means are formed by the conical fitting of a post secured to the head into a recess formed in the respective stem;
- the conical fitting has a Morse taper, that is to say having a cone angle of around 5%: however, this cone angle may also be smaller, for example around 3% or 2.5%;
- the biconcave surface comprises a base provided with a connection post of predetermined thickness.

Providing a base of predetermined thickness thus permits a number of predetermined thicknesses that the surgeon will be able to choose and adapt to the cut made during the operation;

- the attachment means between the parts of an element formed by the stem and the respective head moreover comprise a recess or a groove formed in one of the parts able to receive a plate of complementary shape that is secured to the other part;
- the biconvex bicondylar pivot surface and the respective biconcave surface have uniform radii of curvature in the frontal plane and variable radii of curvature in the sagittal plane;
- the attachment means are identical between on the one hand a plurality of heads of different size and on the other hand identical or different stems of first elements and/or second elements.

Such an arrangement allows a high degree of modularity.

The invention also proposes a method of installing an orthopedic implant for arthroplasty of the fingers, of the type described above.

The invention will be better understood on reading the following description of embodiments that are given below by way of nonlimiting examples. The description refers to the accompanying drawings, in which:

DETAILED DESCRIPTION

Figures 1, 2, 3:
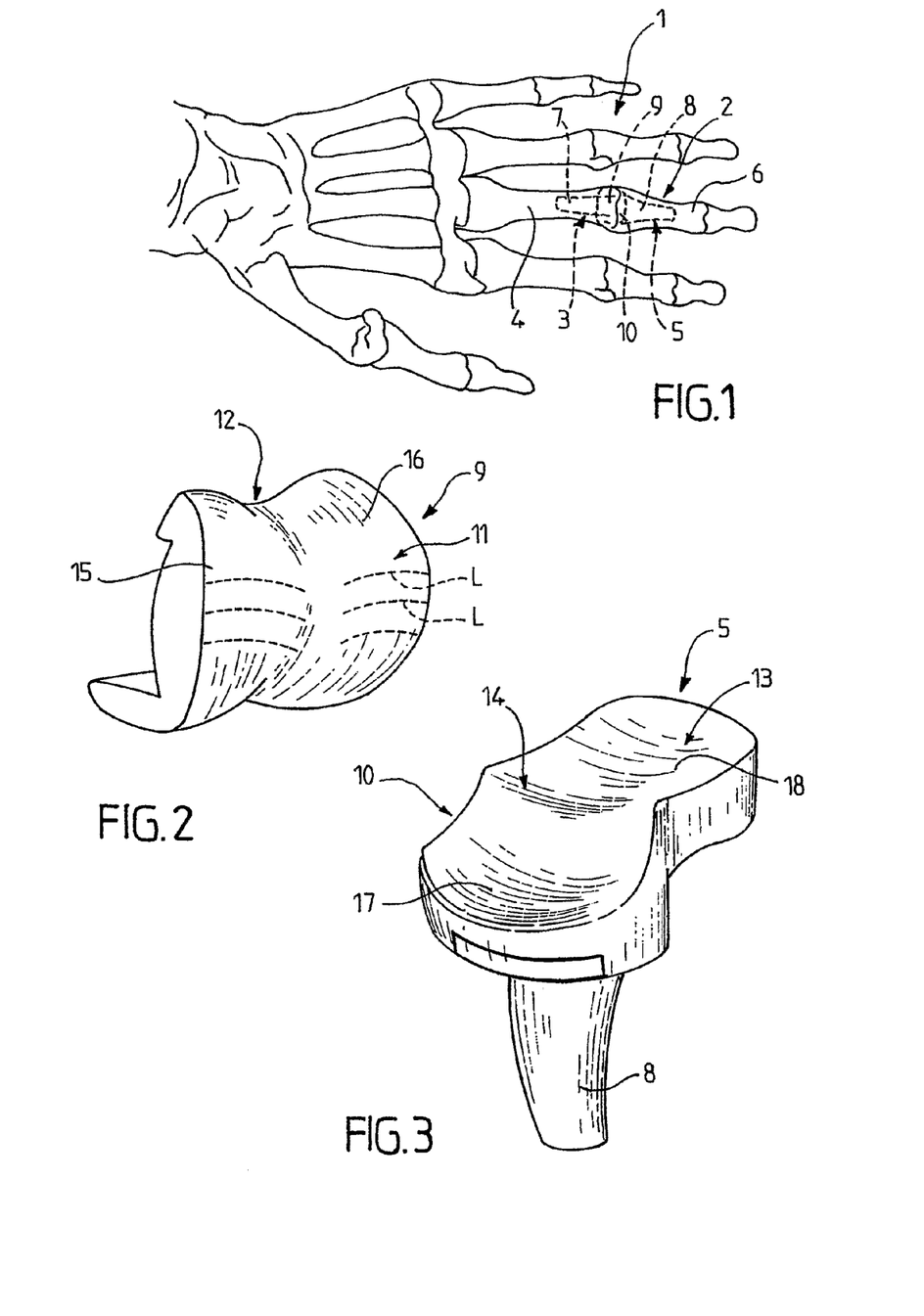
FIG. 1 is a schematic top view of the bones of a hand in which an implant according to the invention has been installed.
FIG. 2 shows in perspective the biconvex head of a first element according to one embodiment of the invention.
FIG. 3 is a perspective view of a second element having a biconcave head designed to cooperate with the head of the first element of FIG. 2.
Figure 4:
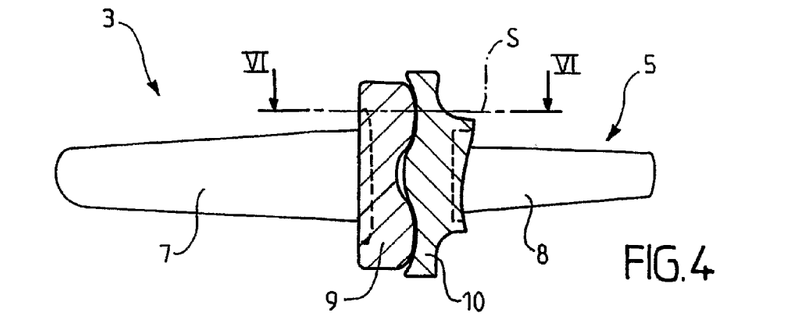
FIG. 4 is a schematic top or dorsal view showing an implant according to the invention, with the joint in the extended position.
Figure 5:
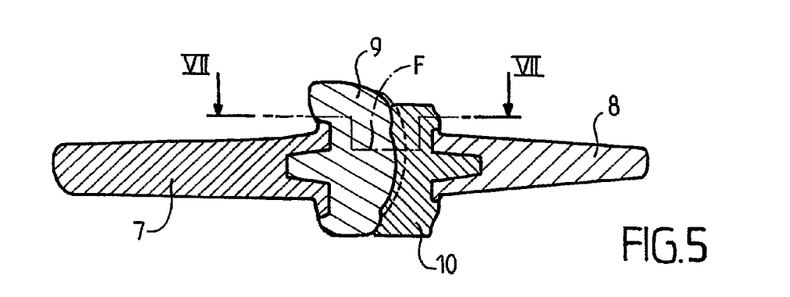
FIG. 5 is a sectional side view of the implant of FIG. 4, with the palmar side facing upward.

FIG. 1 is a schematic top view of a skeletal hand 1, having an orthopedic implant 2 according to the invention;

This implant comprises a first element 3 for a proximal phalanx 4 and a second element 5 for a distal phalanx 6;

Each element comprises a respective stem 7, 8 for implantation in the bone and a respective interphalangeal pivot head 9, 10.

Hereinbelow, the same reference numbers will be used to denote similar or identical elements.

FIG. 2 shows the head 9 of the first element 3.

It has a biconvex condylar pivot surface 11 having a central valley 12.

FIG. 3 for its part shows the second element 5 having an implantation stem 8 and the head 10.

The latter has a biconcave surface 13 designed to cooperate with the biconvex surface 11 of the head of the first element.

This biconcave surface 13 comprises a central ridge 14.

The surfaces 11 and 13 are designed so as to be congruent in the area of the two condyles 15 and 16 and of the respective concave surfaces 17 and 18 in the frontal plane of the pivot and so as not to be congruent in the sagittal plane.

More specifically, FIGS. 4, 5, 6 and 7 show the embodiment more particularly described here of this congruence or of noncongruence.

Figure 7:
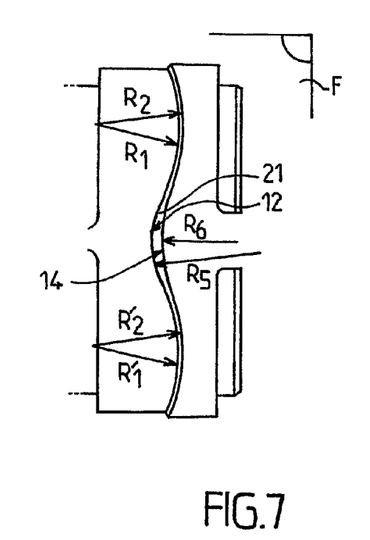

To this end, the surfaces of the condyles and the facing surfaces have radii of curvature such that, with reference to FIG. 7, in the frontal plane F, the radii of curvature R1, R'1 of the condyles having a convex surface are identical or substantially identical to the radii of curvature R2, R'2 of the respective concave surfaces of the second element.

Substantially identical is to be understood to mean a value equal to ±5%.

By contrast, the radius of curvature R3 of the proximal surface of the first element (see FIG. 6) is smaller than the radius of curvature R4 of the respective distal surface of the second element in the sagittal plane S, for example between 1.1 and 1.5 times smaller, for example 1.2 times smaller.

Figure 6:
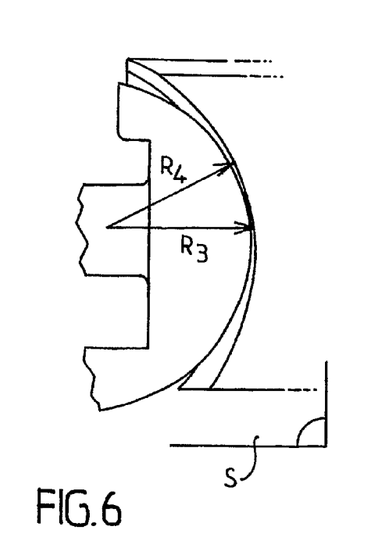
FIGS. 6 and 7 are respectively sectional views along VI-VI and along VII-VII in FIGS. 4 and 5 showing the radii of curvature in the sagittal and frontal planes of the pivot surfaces according to the embodiment of the invention more particularly described here.

This makes it possible to obtain congruences and non-congruences as mentioned above.

For example, R3 is between 3.4 mm (size S), 3.75 mm (size M) and 4.5 mm (size L) for a radius R4=5 mm.

Advantageously, the radii R1, R'1, R2, R'2 are all equal for example to a value between 4 mm and 6 mm, for example 5 mm.

Figure 8:
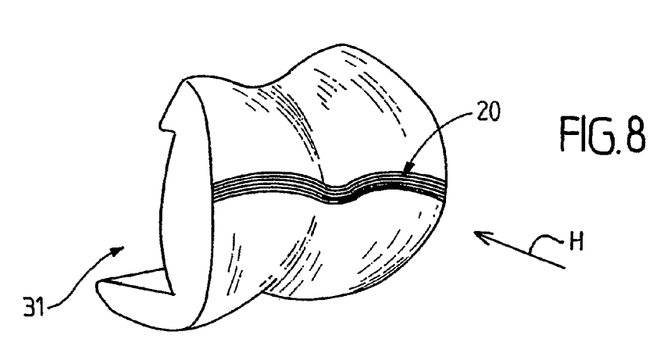
FIG. 8 shows the head of FIG. 2 under longitudinal stress, causing a crush zone to appear in the case of using a more flexible head material according to one embodiment of the invention.

FIG. 8 shows the contact zone 20 obtained with a first element head made from elastic material when a longitudinal pressure (arrow H in FIG. 8) is exerted.

This is because the line of friction in the frontal plane then is applied to a zone 20, which makes it possible to better distribute the friction forces and thus unexpectedly to minimize the long-term wear on the head.

In other words, and by virtue of the combination of the material of this head, which may for example be a polymer of the UHMWPE type, and the respective radii of curvature mentioned above, an excellent damping and minimized wear are thus obtained.

Still with reference to FIGS. 6 and 7, there is provided an intercondylar space 21 of a volume greater than zero along the entire length of the central valley 12 facing the ridge 14, which space facilitates the liquid lubrication, for example a theoretical volume that will depend on the pressure on the prosthesis of around 20 mm$^3$, for example 24 mm$^3$.

To this end, the radius of curvature R5 of the valley and the radius of curvature R6 of the ridge are such that R6 is greater than R5, for example 4.5 mm for the former and 2.5 mm for the latter.

According to the invention more particularly described here, the implant comprises two elements 3 and 5, each provided with a head 9, 10 and with a respective removable stem 7, 8 that can be detached from the head for fixation in the bone.

Figure 8A:
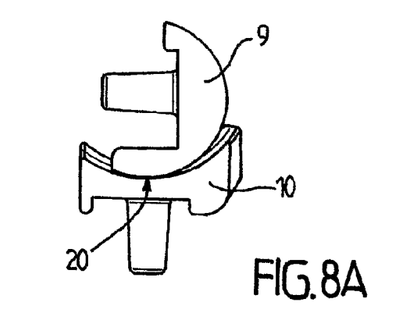
FIGS. 8A and 8B are sectional views of the joint respectively in a position with the finger flexed and with the finger straight, showing the zone of crush contact between the surfaces.
Figure 8B:
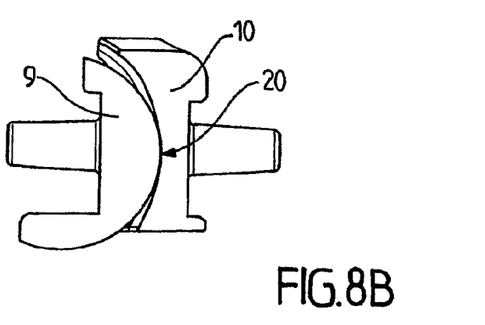

FIGS. 8A and 8B show the change in the zone 20 in the course of the movement, with the finger flexed (FIG. 8A) and with the finger straight (FIG. 8B).

It can be seen that the zone 20 covers half the condyle but remains more or less at the same location on the distal part. The most fragile surface is thus chosen for the condyle side according to the embodiment of the invention more particularly described here.

Figure 9:
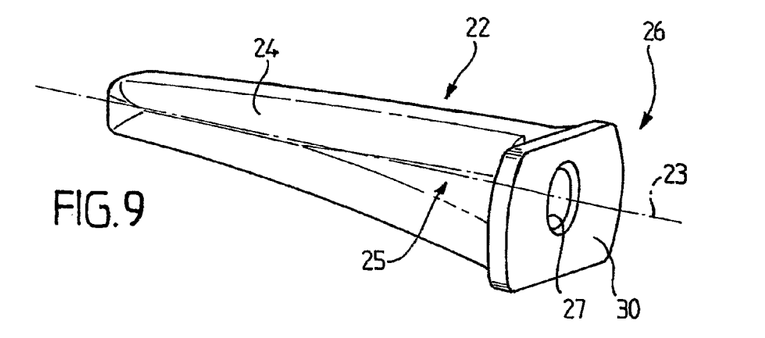
FIG. 9 shows an implant stem that can be used with the head of FIG. 8, according to one embodiment of the invention.

FIG. 9 shows an example of such an implantation stem 22 made from titanium.

The stem 22 has a part elongated substantially around an axis 23, slightly curved, for example with a radius of curvature r of 100 mm for a stem for a proximal element of large size and of 90 mm for a proximal element of medium or small size or between 50 mm (large size), 40 mm (medium size) and 10 mm (small size) for the distal elements.

The stem is provided with a part designed to be fitted into the central hole of the marrow of the phalanx, namely a part 24 of substantially polygonal shape, for example of hexagonal shape with a slightly frustoconical end 25 that enables good introduction and lateral blocking in terms of indexing in the modular cavity of the phalanx.

The implantation stem is removably mounted by attachment means 26 on the head.

These attachment means comprise a conical orifice 27 (see also FIG. 10), into which there is inserted a conically tapered post 28 that is secured to the head 29 and has for example a cone angle of 2 to 3°.

Figure 10:
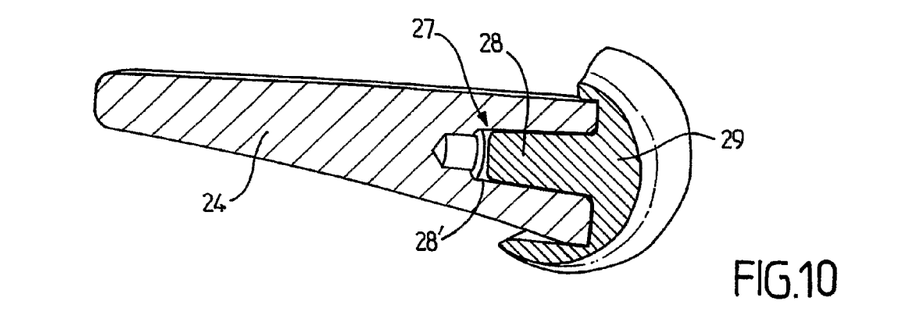
FIG. 10 is a sectional side view of an implant element having a stem and a head according to one embodiment of the invention.

The stem also comprises a stop plate 30 that cooperates with a complementary recess in the form of a groove 31 (see FIG. 8) that allows a good securing and a good indexing of the head 29 to the stem 24 when the post 28 is pushed into the recess 28' and the plate 30 is locked into the recess 31.

On the second element side, advantageously the head 10 has a base (see FIG. 11) 32, 33, of 34 of variable thickness that makes it possible to adjust the thicknesses at the time of installation of the implant so as to optimize functioning of the joint during the surgical operation.

Figure 11:
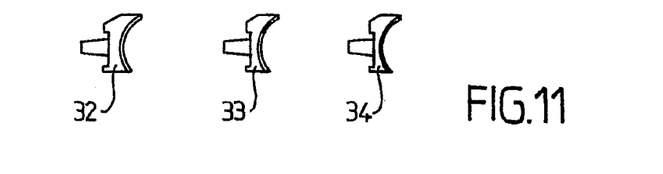
FIG. 11 schematically shows in side view three embodiments of heads for a second element according to the invention, with bases of different thickness.

This base may for example have a thickness of 1 mm, 2 mm; 1.7 mm, or 2.2 mm.

Advantageously, the convex bicondylar pivot surface and the biconcave surface have uniform radii of curvature in the frontal plane and different radii of curvature in the sagittal plane.

The fact of standardizing or of making the dimensions of the posts 28 and of the orifices 27 uniform furthermore makes it possible to adapt indifferently a head of predetermined size to a stem of different size, thereby allowing a high degree of modularity.

Other means of mechanically assembling the head to the stem are of course possible.

The differences in thickness between the different bases may range from 0.5 mm to 1.5 mm per size.

FIGS. 12 to 16 show stems for a distal or proximal element of different shapes and lengths according to embodiments of the invention.

Figure 12:
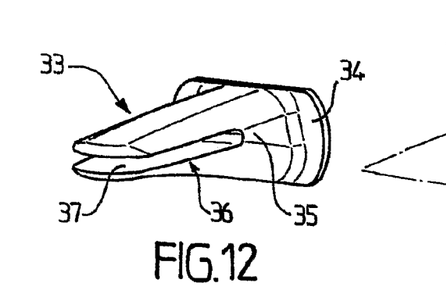
FIGS. 12 to 16 show in perspective from behind five embodiments of a stem for implantation according to the invention.

The stem 33 of FIG. 12 has on one side a stop plate 34 of the type described with reference to FIG. 9, the plate being formed with a throughgoing hole for receiving the post of the head.

The solid part 35 extends away from the plate as a flat beveled portion 36 provided with a slot 37 that is open along its entire length and that is of small thickness, for example 2 mm in the dorsal-palmar plane, which gives it a standard duckbill shape.

Figure 13:
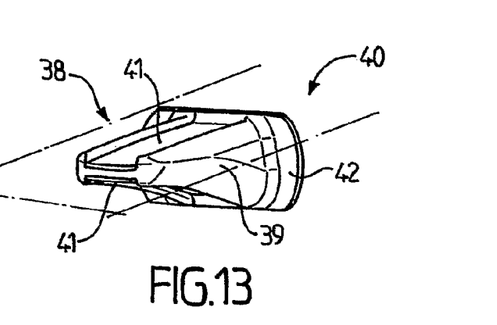

FIG. 13 shows another embodiment of the stem 38 showing a part 39 capable of being pushed into the bone, the part being substantially pyramidal or frustoconical with an H-shaped cross-section, thereby exposing on either side of the dorsal-palmar plane 40 substantially parallelepipedal recesses from the duckbill-shaped end 41 to the stop plate 42.

Figure 14:
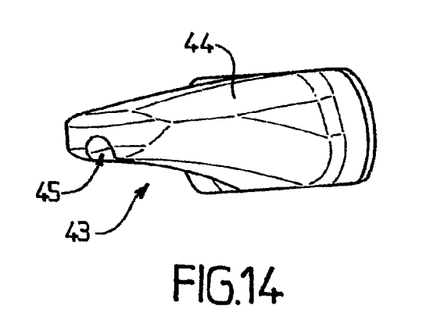

FIG. 14 shows another stem 43 having a part 44 of frustoconical shape provided on its lower surface with a groove 45 that gives the stem a recessed shape.

Figure 15:
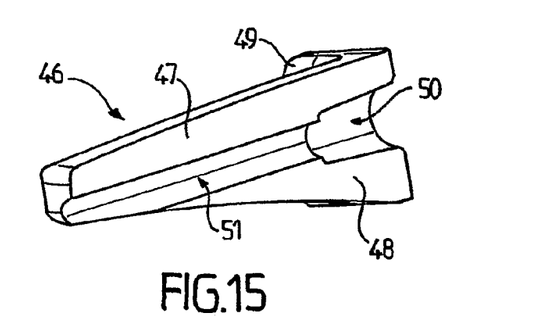

FIG. 15 for its part shows in cross-section a half-stem 46 in the shape of a substantially cylindrical tube 47 having an end 48 provided with the plate 49, formed with a throughgoing hole 50 in order to complementary fit with the post of the head as described above, the opening 50 being extended by a bore 51 along the entire length of the tube 47.

Figure 16:
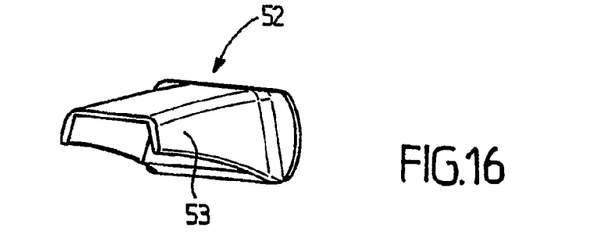

FIG. 16 shows a stem 52 in the shape of a folded sheet, having an end part 53 with a U-shaped cross-section.

In the embodiments of the invention more particularly described here, the stems have rough outer surfaces.

This roughness is obtained for example by blasting with sand or corundum, or by means of transverse fluting (not shown), making it possible to increase the adhesion in the bone.

In order to further improve anchoring, an osseointegrating coating is advantageously provided, for example of the hydroxyapatite (HAP) type or formed from microporous titanium by plasma deposition.

The installation of a prosthesis according to the invention during an implantation operation will now be described.

After opening the finger and cutting away the damaged bone parts in order to install the prosthesis, in a manner known per se, (first bone resection step) the housings for the stems are prepared (introduction of rasps) and then the fixing stem is fitted into the medullary canal.

The space available for the installation of the heads is then verified, and then the proximal condylar head 9 is installed and is fixed onto the stem in a precise and locked manner by way of the Morse cone.

A test is then performed with a phantom of the other distal head.

Then, after choosing the thickness as a function of the prior resection of the bone, the stem 8 is installed on the other side in the distal phalanx and the joint is finalized by installing the head 10.

The fact that the head 10 can have several different thicknesses for its base therefore permits adjustment during the operation.

All of these operations are carried out in a manner known per se using dedicated ancillary equipment.

As will be understood, and as is also clear from the above, the present invention is not limited to the embodiments more particularly described. On the contrary, it encompasses all the is variants and in particular those in which the two heads 9 and 10 are made from flexible material, those in which the stems are made from biocompatible polyethylene or from a metal other than titanium, those in which the prosthesis is a thumb or big toe IP prosthesis, or an IPD prosthesis that involves different dimensions and a different design of the articular surfaces so as to allow adequate lateral mobility.

The invention claimed is:

1. An orthopedic implant used in arthroplasty of the fingers, comprising a first element for implantation in a proximal phalanx and a second element for implantation in an adjacent distal phalanx, each element having a respective stem sized for implantation in the respective phalanx and an interphalangeal pivot head, a head of the first element having a biconvex condylar pivot surface including a central valley having a radius of curvature R5 in the frontal plane, and a head of the second element having a biconcave condylar pivot surface designed to fit generally complementarily with the biconvex condylar pivot surface including a central ridge having a radius of curvature R6 in the frontal plane,
    wherein the biconcave and biconvex condylar pivot surfaces at rest are congruent in the frontal plane and are not congruent in the sagittal plane, and
    wherein radii of curvature R1, R'1 of the biconvex condylar pivot surface of the first element are identical to respective radii of curvature R2, R'2 of the biconcave condylar pivot surface of the second element in the frontal plane, and
    wherein the central valley of the biconvex condylar pivot surface and the central ridge of the biconcave condylar pivot surface define an intercondylar space along a length of the central valley, the intercondylar space having a volume between 15 mm$^3$ and 30 mm$^3$.

2. The orthopedic implant according to claim 1, wherein a radius of curvature of the biconvex condylar pivot surface of the first element is less than or equal to a radius of curvature of the biconcave condylar pivot surface of the second element in the sagittal plane.

3. The implant according to claim 1, wherein the radii of curvature are such that R1=R'1=R2=R'2.

4. The implant according to claim 1, wherein the surfaces and the material of the heads are designed to cooperate by friction along a line of friction in the frontal plane in the absence of longitudinal pressure and along a crush zone in the frontal plane in the event of longitudinal pressure.

5. The implant according to claim 4, wherein the material of the biconvex condylar pivot surface of the head of the first element is a flexible polymer material having a modulus of elasticity E, wherein E≤30 GPa.

6. The implant according to claim 5, wherein the material of the biconvex bicondylar pivot surface has a modulus of elasticity E, wherein E≤2 GPa.

7. The implant according to claim 1, wherein facing surfaces of the heads of the two elements placed in contact define an intercondylar space of a volume greater than zero along the entire length of the central valley, allowing improved lubrication of the joint between the heads.

8. The implant according to claim 7, wherein the radius of curvature R5 of the central valley of the head of the first element is less than the radius of curvature R6 of the central ridge of the second element.

9. The implant according to claim 1, wherein each of the respective implantation stems has a shape of a polygonal post that is proportioned so as to be received inside the medullary cavity of the respective phalanx and is provided with a stop to prevent it from being excessively pushed in.

10. The implant according to claim 1, wherein at least one of the respective implantation stems has a shape that is at least partially open in a dorsal-palmar plane.

11. The implant according to claim 10, wherein at least one of the respective implantation stems has one of a U-shaped, an H-shaped, and a V-shaped cross-section.

12. The implant according to claim 10, wherein at least one of the respective implantation stems has a recessed semicylindrical shape on the palmar side or a half-tube shape.

13. The implant according to claim 1, wherein at least one of the respective implantation stems of the first and second elements includes a means for attachment to the respective head of the first and second elements such that the at least one respective implantation stem is removable relative to the respective head.

14. The implant according to claim 13, wherein the attachment means are formed by a conical fitting of a post secured to the head into a recess formed in the at least one respective implantation stem.

15. The implant according to claim 14, wherein the conical fitting has a Morse taper.

16. The implant according to claim 13 wherein the biconcave surface includes a base provided with an attachment post of predetermined thickness.

17. The implant according to claim 13, wherein the attachment means includes a recess or a groove formed in one of a stem and a respective head able to receive a plate of complementary shape that is secured to the other of the stem and the respective head.

18. The implant according to claim 1, wherein the biconvex condylar pivot surface and the respective biconcave condylar pivot surface have uniform radii of curvature in the frontal plane and variable radii of curvature in the sagittal plane.

19. A set of implants according to claim 13, the set of implants including a plurality of heads and a plurality of stems, each head and each stem corresponding to one of the first and second elements,
wherein the plurality of heads includes heads of different sizes and the plurality of stems includes substantially identical or different stems, and
wherein the attachment means of each implant of the set of implants is substantially identical between each head of the plurality of heads and each stem of the plurality of stems corresponding to the first element and each head of the plurality of heads and each stem of the plurality of stems corresponding to the second element.

20. The implant according to claim 2, wherein a radius of curvature of the biconvex condylar pivot surface of the first element is less than 1.2 times smaller than a radius of curvature of the biconcave condylar pivot surface of the second element in the sagittal plane.

* * * * *